US010548628B2

(12) United States Patent
Swaney et al.

(10) Patent No.: US 10,548,628 B2
(45) Date of Patent: Feb. 4, 2020

(54) STEERABLE SURGICAL NEEDLE

(71) Applicant: Vanderbilt University, Nashville, TN (US)

(72) Inventors: Philip J. Swaney, Nashville, TN (US); Robert J. Webster, III, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 1261 days.

(21) Appl. No.: 14/208,508

(22) Filed: Mar. 13, 2014

(65) Prior Publication Data

US 2014/0276586 A1 Sep. 18, 2014

Related U.S. Application Data

(60) Provisional application No. 61/787,034, filed on Mar. 15, 2013.

(51) Int. Cl.

*A61B 17/34* (2006.01)
*A61B 17/00* (2006.01)
*A61N 5/10* (2006.01)

(52) U.S. Cl.

CPC ...... *A61B 17/3403* (2013.01); *A61B 17/3417* (2013.01); *A61B 2017/003* (2013.01); *A61B 2017/3454* (2013.01); *A61N 5/1007* (2013.01)

(58) Field of Classification Search

CPC ............ A61B 17/3403; A61B 17/3417; A61B 2017/00305; A61B 2017/003; A61B 2017/3454; A61B 17/3401; A61B 2017/3405; A61B 2017/3407; A61B 2017/3409; A61B 2017/3411; A61B 2017/3413

USPC .......................................... 606/185; 604/528

See application file for complete search history.

(56) References Cited

U.S. PATENT DOCUMENTS 4,235,238 A * 11/1980 Ogiu ...................... A61B 17/04 606/145
5,531,677 A * 7/1996 Lundquist .......... A61B 10/0233 604/164.08
6,371,943 B1 4/2002 Racz et al.
7,435,240 B2 10/2008 Barkhahn et al.
7,641,638 B2 1/2010 Waxman et al.
2003/0032927 A1 2/2003 Halseth et al.
2008/0097347 A1 4/2008 Arvanaghi (Continued)

OTHER PUBLICATIONS

N. Abolhassani, R. Patel and M. Moallem, "Needle Insertion into Soft Tissue: A Survey," Medical Engineering & Physics, vol. 29, 2007, pp. 413-431.

(Continued)

*Primary Examiner* — Erich G Herbermann

(74) *Attorney, Agent, or Firm* — Tarolli, Sundheim, Covell & Tummino LLP

(57) ABSTRACT

A steerable surgical needle (10) includes an elongated needle shaft (12), a beveled tip portion (14), and a flexural element (16) that connects the needle shaft (12) with the tip portion (14) and permits the tip portion to deflect relative to the needle shaft. A method for steering the surgical needle (10) through tissue includes the steps of advancing the needle in the body tissue to induce tip flexure which causes the needle to follow a curved trajectory, and rotating the needle about its longitudinal axis in place, without advancement, to remove the tip flexure.

27 Claims, 4 Drawing Sheets

Z
Y
X
12
3A
40
10
14
3B
22
16,44
18
3A
20
3B

(56) References Cited

U.S. PATENT DOCUMENTS

| | | | | |
|---|---|---|---|---|
| 2009/0024110 | A1* | 1/2009 | Heideman | A61M 25/0012 604/528 |
| 2010/0106177 | A1* | 4/2010 | Chanduszko | A61B 17/0057 606/185 |
| 2012/0191090 | A1* | 7/2012 | Sugahara | A61B 17/00234 606/45 |
| 2012/0265186 | A1* | 10/2012 | Burger | A61B 17/8811 606/21 |
| 2012/0265210 | A1* | 10/2012 | Grinberg | A61B 17/8811 606/93 |

OTHER PUBLICATIONS

R. Alterovitz, M. Branicky and K. Goldberg, "Motion Planning Under Uncertainity for Image-Guided Medical Needle Steering," The International Journal of Robotics Research, vol. 27, No. 11-12, 2008, pp. 1361-1374.

V. Kallem and N.J. Cowan, "Image Guidance of Flexible Tip-Steerable Needles," IEEE Transactions on Robotics, vol. 25, No. 1, 2009, pp. 191-196.

J. Xu, V. Duindam, R. Alterovitz, J. Pouliot, J. Adam, M. Cunha, I. Hsu and K. Goldberg, "Planning Fireworks Trajectories for Steerable Medical Needles to Reduce Patient Trauma," IEEE/RSJ International Conference on Intelligent Robots and Systems, Oct. 11-15, 2009, pp. 4517-4522.

T.R. Wedlick and A. M. Okamura, "Characterization of Pre-Curved Needles for Steering in Tissue," 31st Annual International Conference of IEEE EMBS, Sep. 2-6, 2009, pp. 1200-1203.

S. Misra, K. B. Reed, B.W. Schafer, K.T. Ramesh and A.M. Okamura, "Mechanics of Flexible Needles Robotically Steered through Soft Tissue," Int. J. Rob. Res., 2009, pp. 1640-1660.

K. B. Reed, A. Majewicz, V. Kallem, R. Alterovitz, K. Goldberg, N.J. Cowan and A.M. Okamura, "Robot-Assisted Needle Steering," IEEE Robotics & Automation Magazine, 2011, pp. 35-46.

S. Okazawa, R. Ebrahimi, J. Chuang, S.E. Salcudean, and R. Rohling, "Hand-Held Steerable Needle Device," IEEE/ASME Transactions on Mechatronics, vol. 10, No. 3, 2005, pp. 285-296.

A. Asadian, M.R. Kermani, and R.V. Patel, "A Novel Force Modeling Scheme for Needle Insertion Using Multiple Kalman Filters," IEEE Transactions on Instrumentation and Measurement, vol. 61, No. 2, 2012, pp. 429-438.

A. Asadian, M. R. Kermani, and R.V. Patel, "Robot-Assisted Needle Steering Using a Control Theoretic Approach," J. Intell Robot Syst., 2011 pp. 397-418.

D.S. Minhas, J.A. Engh, M.M. Fenske, and C.N. Riviere, "Modeling of Needle Steering via Duty-Cycled Spinning," Proceedings of the 29th Annual International Conference of IEEE EMBS, Aug. 23-26, 2007, pp. 2756-2759.

J.A. Engh, G. Podnar, D. Kondziokla, and C.N. Riviere, "Towerd Effective Needle Steering in Brian Tissue," Proceedings of the 28th IEEE EMBS Annual International Conference, Aug. 30-Sep. 3, 2006, pp. 559-562.

L. Frasson, S.Y. Ko, A. Turner, T. Parittotokkaporn, J.F. Vincent, and F. Rodriguez Y Banena, "STING: A Soft-Tissue Intervention and Neurosurgical Guide to Access Deep Brain Lesions Through Curved Trajectories," Proc. IMechE. vol. 224, part H:J, Engineering in Medicine, 2009, pp. 775-788.

R.J. Webster, III, J. Memisevic, and A.M. Okamura, "Design Considerations for Robotic Needle Steering," Proceedings of the 2005 IEEE International Conference on Robotics and Automation, Apr. 2005, pp. 3588-3594.

R. Webster, III, J.S. Kim, N.J. Cowan, G.S. Chirikjian and A.M. Okamura, "Nonholonomic Modeling of Needle Steering," The International Journal of Robotics Research, vol. 25, No. 5-6, 2006, pp. 509-525.

* cited by examiner

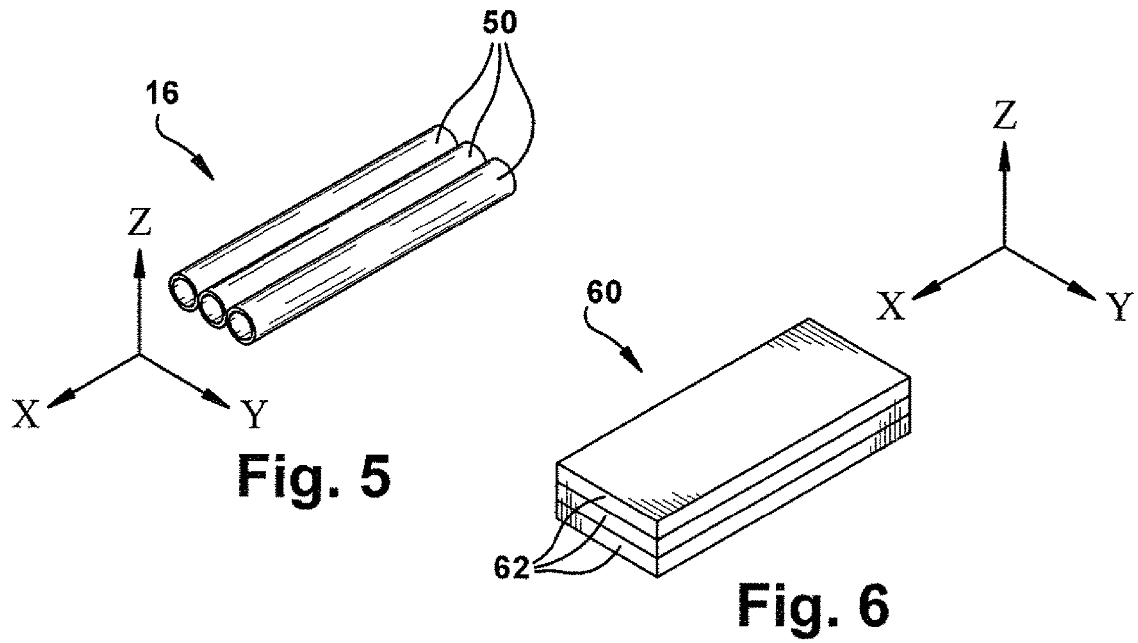
Fig. 5
Fig. 6
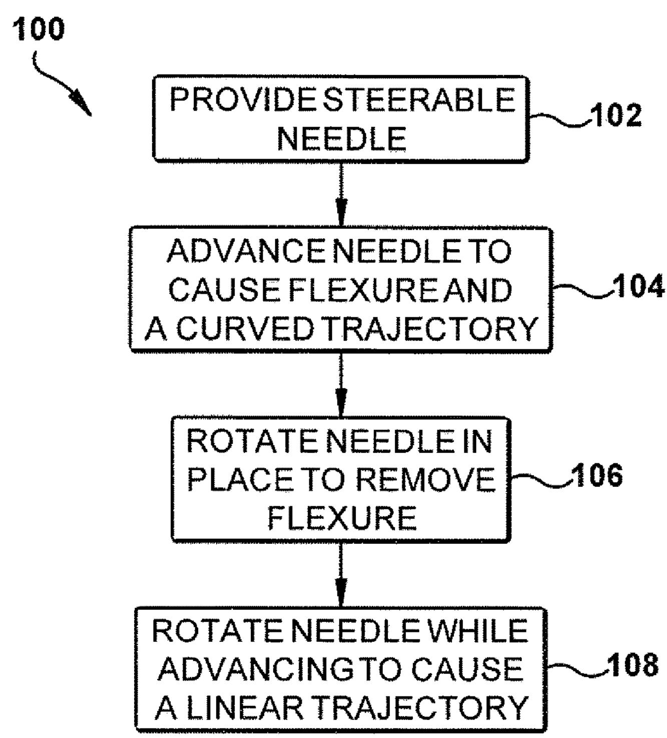
Fig. 7

STEERABLE SURGICAL NEEDLE

RELATED APPLICATION

This application claims the benefit of U.S. Provisional Application Ser. No. 61/787,034, which was filed on Mar. 15, 2013.

GOVERNMENT RIGHTS

This invention was made with government support under National Science Foundation Career Award Grant No. IIS-1054331. The government has certain rights in the invention.

This invention was made with government support under grant numbers DGE0909667 and IIS1054331 8 awarded by the National Science Foundation and under grant number EB01162 awarded by the National Institutes of Health. The government has certain rights in the invention.

TECHNICAL FIELD

The invention relates to surgical needles for percutaneous medical procedures. More specifically, the invention relates to steerable surgical needles for navigating a path to reach a target location in a body tissue.

BACKGROUND

Surgical needles can be used in a variety of percutaneous medical procedures, such as diagnosing a condition (e.g., biopsy) and delivering a treatment or therapy (e.g., drug delivery, thermal ablation (heat or cold), brachytherapy, and targeted doses of chemotherapy or radiotherapy) to a target location in the patient. The effectiveness of such diagnoses and treatments is strongly correlated with the accuracy with which the needle tip is placed at the desired target location. Conventional free-hand needle placement involves manipulating a visualization system (e.g., an ultrasound probe) while simultaneously inserting and advancing the needle, which requires the physician to mentally relate the images on a video screen to locations inside the patient.

There are numerous factors that can contribute to needle placement inaccuracy. Example factors include tissue deformation, registration error, and the surgeon's hand-eye coordination. There are also situations where a straight-line path to the surgical site is not possible because of anatomical constraints. Examples include deep brain stimulation, where certain targets can be obstructed by eloquent brain tissue and transperineal prostate brachytherapy, where the pubic arch can sometimes obstruct a portion of the prostate. It may also be desirable to reach multiple sites within the target area without full retraction of the needle. In these situations, it may be desirable to steer the needle to navigate a desired needle trajectory.

Surgical needles have a beveled tip that generates bending forces as the needle is advanced into tissue. If the needle is flexible, the bending forces generated by the beveled tip cause the needle to follow a curved path. These bending forces can be harnessed to steer the needle to a target location in the tissue. Steering is achieved by controlling the insertion/advancing velocity of the needle (i.e., along the longitudinal axis of the needle) and the rotation velocity of the needle (i.e., about the longitudinal axis of the needle). Control of these variables is achieved by duty cycling.

Duty cycling adjusts the curved trajectory of the advancing needle by alternating between periods of insertion without rotation and periods of insertion with rotation. When the flexible bevel tip needle is inserted without rotation, the needle follows a trajectory with some natural curvature that is dependent on needle characteristics (e.g., stiffness and bevel angle) and tissue characteristics (e.g., density, consistency, homogeneity). When the needle is advanced with a sufficient rotational velocity, straight trajectories can be achieved. Trajectories ranging from naturally curved to straight (zero curve) can be achieved by combining periods of rotation with periods of non-rotation, i.e., duty cycling.

In the field of steerable surgical needles, "duty cycling" refers to the amount of time that the needle rotates stated as a percentage of total needle advancement time. Thus, for example, if the needle is advanced with a 25% duty cycle, it would be advanced under rotation 25% of the time and without rotation 75% of the time. Duty cycling the needle can be periodic in that the total advancement time can be broken down in to periods, e.g., seconds or fractions thereof, and the duty cycling can occur within those periods.

Robotic systems are ideally suited for duty cycling steerable needles because of their ability to apply constant insertion/advancing and rotational velocities. Robotic systems also have the potential to improve the accuracy of needle tip placement through accurate needle alignment using spatial registration, and can perform tasks rapidly with both accuracy and repeatability. However, even perfect pre-entry alignment cannot guarantee accurate tip placement. Errors can arise due to unforeseen variables, such as deflection at membranes, tissue deformation, non-homogeneous tissue, registration and calibration tolerances, etc. The only way to compensate for these errors is to correct the trajectory by steering the needle. Additionally, the needle can be steered to maneuver around sensitive structures to reach locations where straight trajectories may not be feasible or desirable.

Steering the surgical needle by duty cycling lends well to robotic systems because these systems can implement control algorithms that adjust the duty cycle to steer the needle along desired trajectories. This robotic needle steering can be performed, for example, using image guidance feedback to monitor performance and to calculate adjustments in real time.

Straight beveled tip flexible shaft needles may not yield the degree of curvature necessary to effectuate a desired degree of steerability. To improve the curvature, kinked tip needles have been configured with a bend or kink near the beveled tip. The natural trajectory of a kinked beveled tip needle has a higher degree of curvature than the straight beveled tip needle. This higher degree of curvature improves the steerability of the needle through duty cycling.

Kinked tip needle configurations do have some drawbacks. Since straight trajectories are achieved through simultaneous needle rotation and longitudinal advancement, and due to the rigid bend in the needle shaft, the kinked tip cuts a helical path through the tissue. This helical path has a diameter that is larger than the diameter of the needle shaft and can thus cause undesirable damage to the tissue.

SUMMARY

The invention relates to a steerable surgical needle that includes an elongated needle shaft, a beveled tip portion, and at least one flexural element that connects the needle shaft with the tip portion.

The present invention also relates to a method for steering through tissue with a surgical needle having an elongated needle shaft and a beveled tip that is deflectable relative to the needle shaft. The method includes the step of advancing the needle in the body tissue to induce tip flexure which causes the needle to follow a curved trajectory. The method also includes the step of rotating the needle about its longitudinal axis in place, without advancement, to remove the tip flexure.

DESCRIPTION OF DRAWINGS

FIG. 5 is a schematic view of a portion of the surgical needle of FIGS. 1-4B.

FIG. 6 is a schematic view of an alternative construction of the portion of FIG. 5.

FIG. 7 is a block diagram illustrating a method for using the surgical needle of FIGS. 1-6.

DESCRIPTION

Figure 1:
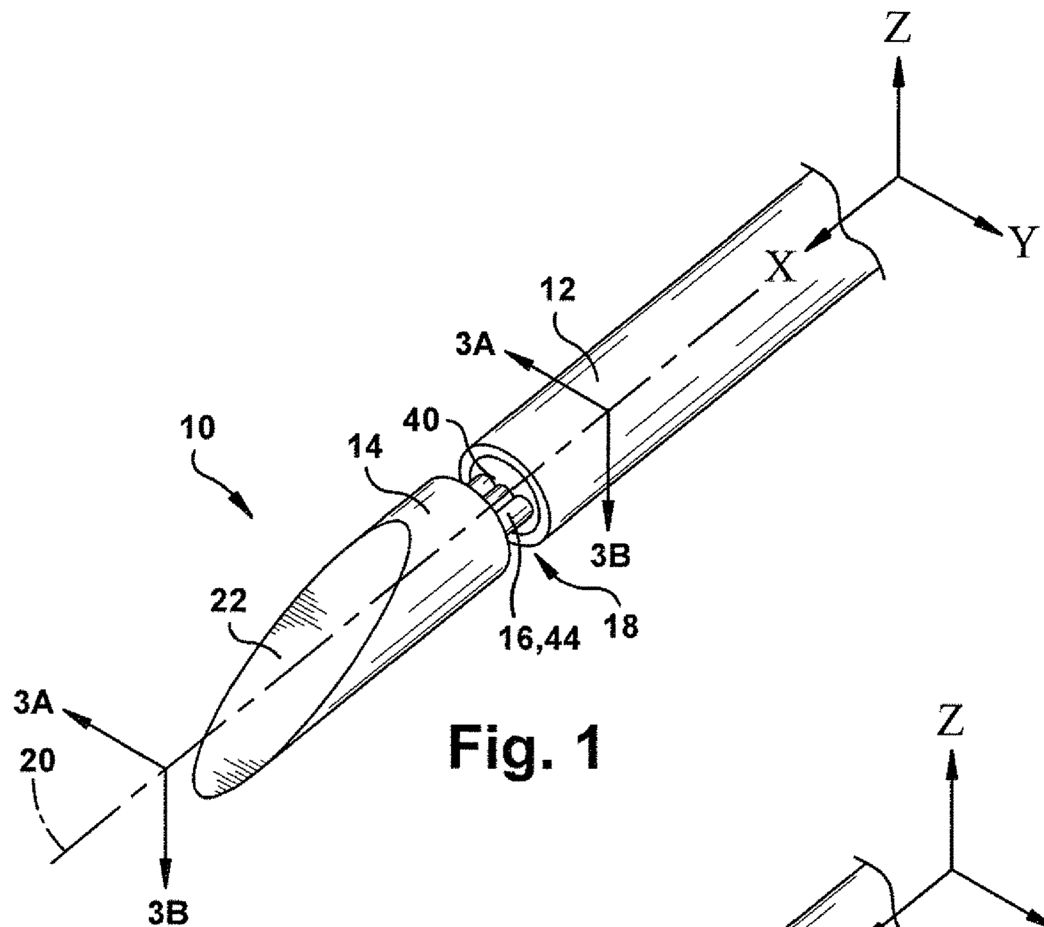
FIG. 1 is a perspective view of a surgical needle.
Figure 2:
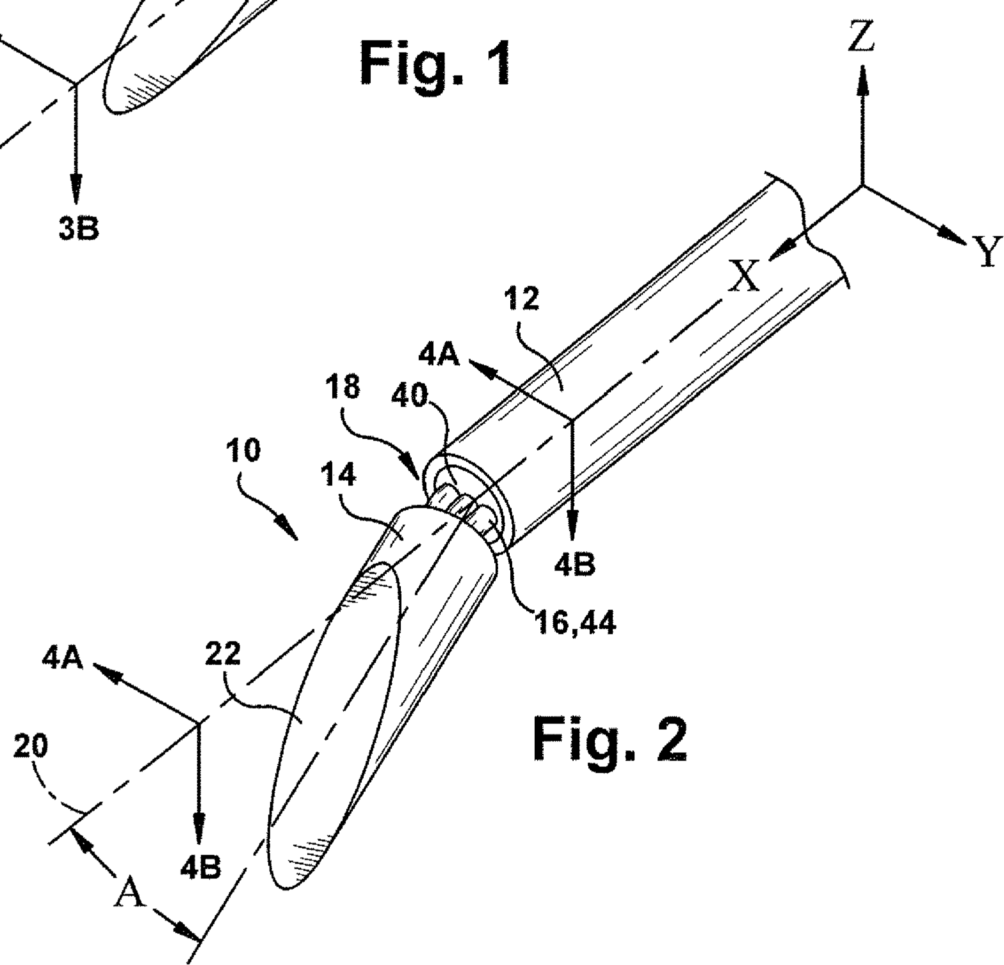
FIG. 2 is a perspective view of the surgical needle of FIG. 1 in a different condition.
Figure 3A:
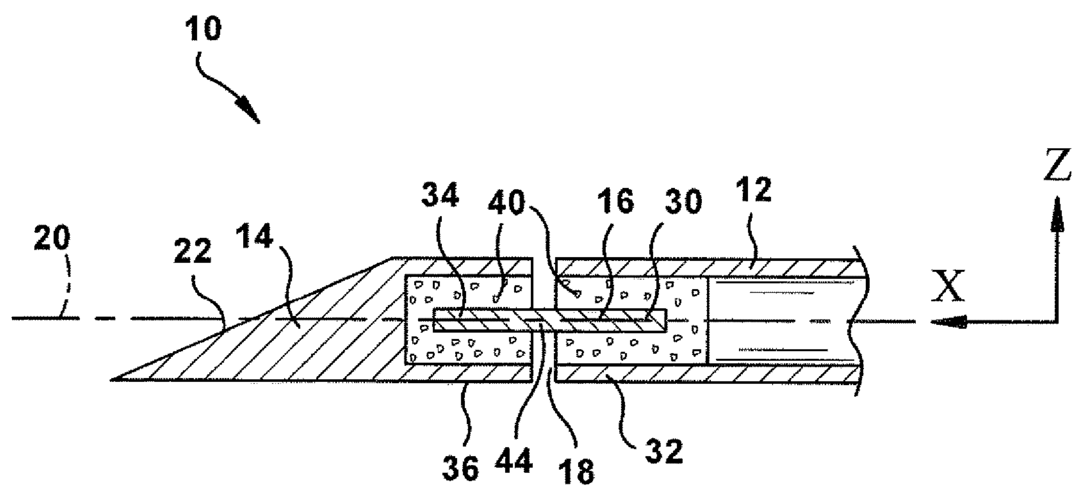
FIGS. 3A and 3B are sectional views taken along lines 3A-3A and 3B-3B, respectively, in FIG. 1
Figure 3B:
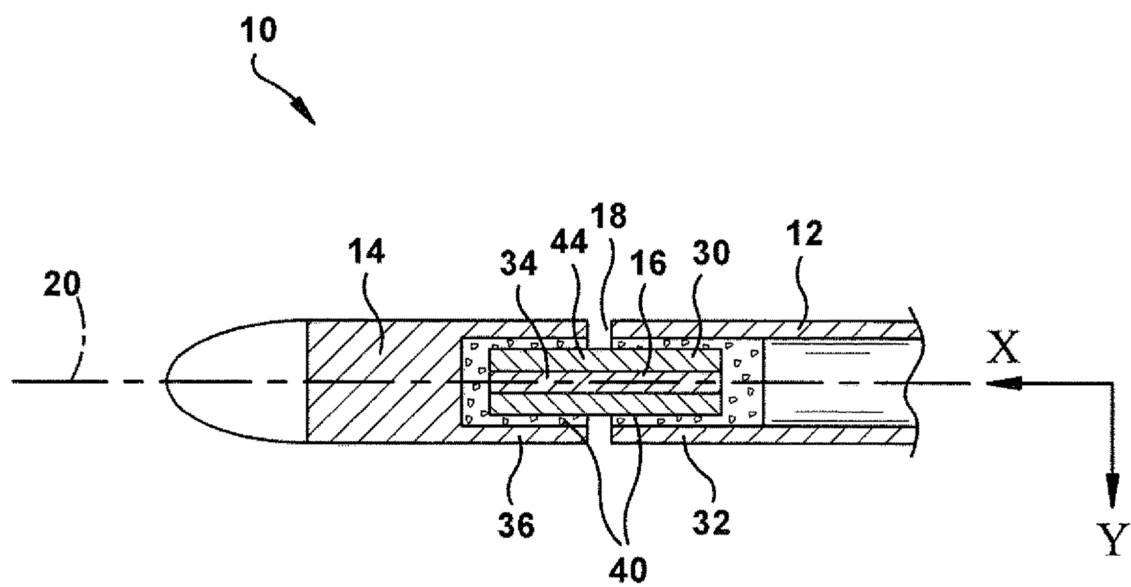
Figure 4A:
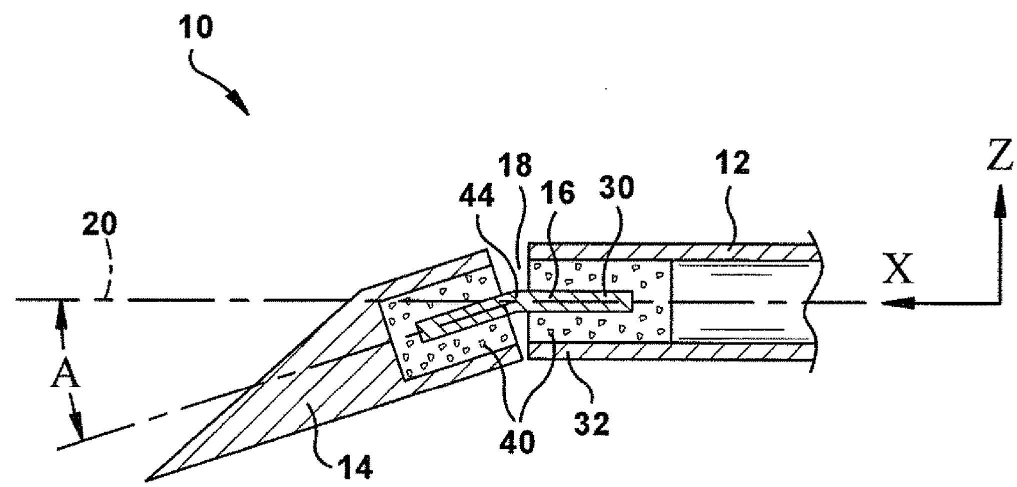
FIGS. 4A and 4B are sectional views taken along lines 4A-4A and 4B-4B, respectively, in FIG. 2.
Figure 4B:
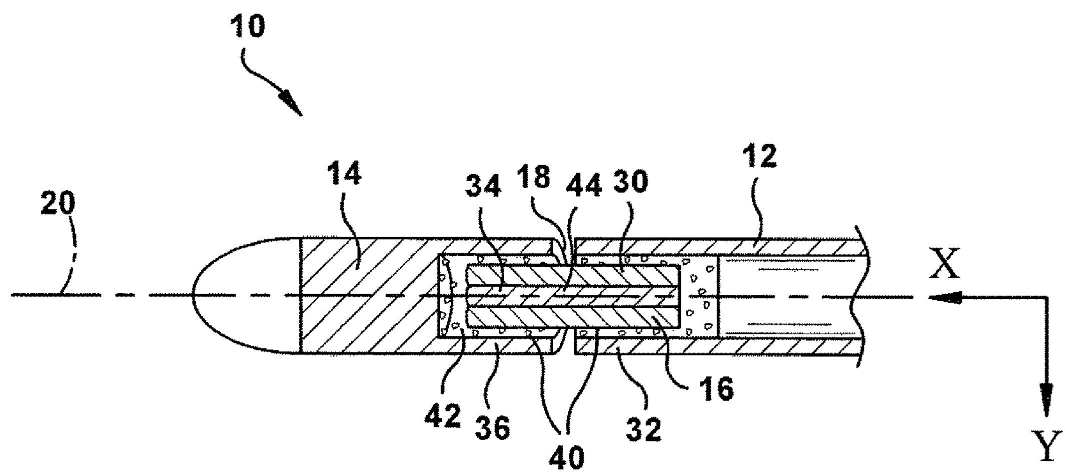

FIGS. 1 and 2 illustrate an example embodiment of a steerable surgical needle 10 according to the invention. The needle 10 includes an elongated main body portion 12, referred to herein as a "shaft" or "needle shaft," and a separate distal end portion 14 including a beveled surface 22, referred to herein as a "tip" or "beveled tip." The needle shaft 12 and the beveled tip 14 are connected to each other by a flexure element 16, referred to herein as a "flexure" or "flex" joint. The needle 10 thus as a flexible tip ("flex-tip") configuration.

The needle shaft 12 is a flexible elongated member that can have a length of up to several meters. The needle shaft 12 is constructed of a biocompatible material that has an elasticity selected to provide the shaft with requisite degree of flexibility. The needle shaft 12 could, for example, be constructed of a stainless steel alloy or a nickel-titanium (nitinol) alloy. In one example construction, the needle shaft 12 is made of a nickel-titanium (nitinol) alloy. Nitinol is highly elastic and has excellent shape memory properties. Thus, with the nitinol construction, the needle shaft 12 can bend or flex freely when acted upon by external forces and will return to its original form, without deformation, after the forces are removed. The needle shaft 12 can have various configurations, such as a hollow tubular configuration, a solid (e.g., wire) configuration, a wound stranded (e.g., cable) configuration, or a combination of these configurations.

The beveled tip 14 has a bevel 22 that forms a sharpened distal end of the needle 10. The beveled tip 14 is also constructed of a biocompatible material. The beveled tip 14 can be constructed of nitinol but, since flexibility is not required, materials such as stainless steel are also suitable. In fact, a stainless steel construction can be advantageous in that it can have a hardness selected to maintain a sharpness of the bevel 22. The beveled tip 14 can have a solid or hollow configuration.

The needle shaft 12 extends along a central needle axis 20. In this description, the needle axis 20 follows the needle shaft 12, i.e., the axis is considered to bend or flex with the shaft. Thus, the needle shaft 12 remains centered on the axis 20 at all times, whether straight or bent.

The flex joint 16 interconnects the beveled tip 14 to the needle shaft 12 and permits the tip to pivot, bend, flex, or otherwise deflect relative to the shaft. The beveled tip 14 and needle shaft 12 are separated by a gap 18. In a non-flexed condition shown in FIG. 1, the needle shaft 12, beveled tip 14, and flex joint 16 extend coaxially along the axis 20. As shown in FIG. 2, the beveled tip 14 and flex joint 16 deviate from the axis 20 at an angle A when the tip flexes relative to the shaft. Thus, the flex-tip construction of the surgical needle 10 allows the needle to transition between a non-flexed condition (FIG. 1) in which the needle has the form of a straight beveled needle, and a flexed condition (FIG. 2) in which the needle has the form of a kinked tip needle. The flex joint 16 can have a resilient construction such that the needle 10 will return to the non-flexed condition (see FIG. 1) on its own upon the removal of forces placing the needle in the flexed condition (see FIG. 2).

Referring to FIGS. 3A-3B and 4A-4B, in an example construction of the needle 10, the needle shaft 12 has a hollow tubular nitinol construction, and the beveled tip 14 has a solid wire stainless steel construction. The flex joint 16 has a first end portion 30 connected to a terminal end portion 32 of the needle shaft 12 and a second end portion 34 connected to a rear end portion 36 of the beveled tip 14. In this embodiment, a cold weld epoxy material 40 fills the terminal end portion 32 of the needle shaft 12, surrounding the flex joint 16 and thereby bonding the flex joint to the shaft. Similarly, the cold weld epoxy material 40 fills a recess 42 in the rear end portion 36 of the beveled tip 14, surrounding the flex joint 16 and thereby bonding the flex joint to the tip. Alternative means of connection, such as welding or mechanical fastening could be used to make these connections, depending on the material construction and configuration of the needle shaft 12, beveled tip 14, and flex joint 16.

In this description, relative movement (La, flexure) of the beveled tip 14 and the needle shaft 12 are described with reference to a 3-D space defined by X, Y, and Z axes and planes defined by those axes. In describing the needle 10 in this context, the shaft axis 20 can be characterized as extending coaxially with the X-axis at the location where the flexure occurs, i.e., at the central portion 44 of the flex joint 16 that spans between the needle shaft 12 and the beveled tip 14. As shown in the figures, the Y-axis and Z-axis extend perpendicular to the X-axis and perpendicular to each other.

The flex joint 16 is configured to permit the beveled tip 14 to flex, or bend, or otherwise deflect relative to the needle shaft 12 in the X-Z plane, i.e., about Y-axis, and to inhibit or resist flexure, bending, deflection in the X-Y plane, i.e., about the Z-axis. This is because the flex joint 16 is constructed to have a stiffness in the X-Y plane that is greater than the stiffness of the flex joint in the X-Z plane. Of course, the flex joint 16 does offer some resistance to flexure in the X-Z plane due to its inherent resilient material properties. Likewise, the flex joint 16 would permit some flexure in the X-Y plane if the bending force has a sufficient magnitude to overcome the bending resistance in that plane. Considered within the confines of advancing the needle 10 through human or animal tissue, however, the flex joint 16 offers a comparatively low stiffness and correspondingly low resistance to flexure in the X-Z plane, and a comparatively high stiffness and correspondingly high resistance to flexure in the X-Y plane.

The flexural properties, i.e., stiffness, of the flex joint 16 in the X-Z plane and the X-Y plane is dependent upon the construction of the flex joint. Factors that can affect the flexural properties of the flex joint 16 are the material used to construct the joint and the configuration of the joint itself. Since the flex joint 16 is essentially a beam that interconnects the needle shaft 12 and the beveled tip 14, it is the cross-sectional configuration of the flex joint that affects the flexural properties of the joint.

In the example embodiment of FIGS. 1-4B, the flex joint 16 has a construction that is detailed schematically in FIG. 5. Referring to FIG. 5., the flex joint 16 is constructed of three solid flexible elements in the form of nitinol rods or wires 50 that are arranged in a parallel and side-by-side (i.e., coplanar) manner. The use of a nitinol material to construct the flex joint 16, due to its superelasticity and shape-memory properties, lends well to its inherent resilient tendency to return the needle to the non-flexed condition upon the removal of forces placing the needle in the flexed condition.

In the example of FIG. 5, there are three nitinol wires 50. The number of wires 50 could, however, be greater or less than three (i.e., one or more). The wires 50 are held in this arrangement by the cold weld epoxy material 40 (see FIGS. 1-4B) that secures the flex joint 16 to the beveled tip 14 and the needle shaft 12. The wires 50 may also be bonded to each other by means (not shown) such as an adhesive.

The wires 50 act in concert to define the flex joint 16 in the form of a beam. It is easy to see that this beam construction of the flex joint 16, viewed in cross-section, is thin in the X-Z plane (see FIG. 3A) and thick in the X-Y plane (see FIG. 3B). It thus follows that the flex joint 16 has a stiffness that is greater in the X-Y plane than in the X-Z plane. The flex joint 16 thus offers flexure in the X-Z plane and resists flexure in the X-Y plane. It is through this construction that the flex joint 16 offers a similar degree of X-Z flexure and X-Y resistance to flexure/bending/deflection between the beveled tip 14 and needle shaft 12.

The flex joint 16 could have alternative constructions. For example, as shown in FIG. 6, a flex joint 60 can be formed from one or more lengths of plate or band material 62, such as stainless steel (e.g., a stainless spring steel), that are positioned overlying each other in the form of a beam. The overlying pieces of material 62 could be bonded, e.g., laminated to each other. In the example of FIG. 6, there are three pieces of overlying material 62. The number of pieces could, however, be greater or less than three. The bands 62 act in concert to define the flex joint 60 in the form of a beam that less stiff/offers flexure in the X-Z plane and that has a greater stiffness/resists flexure in the X-Y plane. It is through this construction that the flex joint 60 can offer a similar degree of X-Z flexure and X-Y resistance to flexure between the beveled tip 14 and needle shaft 12.

From this, those skilled in the art will appreciate that the stiffness and flexural properties of the flex joint 16 can be determined through the selection of the material used to construct the joint and through the configuration, e.g., the cross-sectional shape of the joint. For example, although the flex joints of FIGS. 5 and 6 are illustrated as having metal constructions, alternative materials, such as biocompatible polymers could be used to form the flex joint. Additionally, although the flex joints are illustrated as being constructed of multiple elements positioned adjacent to each other to form a beam having a generally uniform cross-section, the flex joint could have a homogeneous material construction with a cross sectional shape selected to provide the desired flexural properties. A basic example of this principal would be a polymeric flex joint that is molded, extruded, or otherwise formed to have a cross-sectional configuration selected to produce the desired degree of flexure.

According to the flex-tip needle configuration of the invention, the flex joint 16 is configured to place the needle 10 in the flexed condition when advanced without rotation due to forces acting on the bevel 22 of the beveled tip 14. During needle advancement without rotation, body tissue exerts forces normal to the bevel, which urge the beveled tip 14 to flex about the flex joint 16 relative to the needle shaft 12 in the X-Z plane. This places the needle 10 in the flexed condition (FIGS. 3A-B) which mimics the configuration of a conventional kinked tip needle. In the flexed condition, the needle 10 acts in the manner of the conventional kinked tip needle and thereby follows a more curved trajectory as the needle is advanced without rotation.

Additionally, according to the flex-tip needle configuration of the invention, the flex joint 16 is configured to place the needle 10 in the non-flexed condition in response to needle rotation without advancement. When the needle 10 is in the flexed condition and is rotated about the axis 20 without advancement, the surrounding tissues in combination with the needle construction cause the flex joint 16 to bend back toward the non-flexed condition.

Thus, when duty cycling to advance the needle 10 along a desired trajectory, the needle can be placed in the flexed condition to take advantage of the resulting high curvature trajectory; and the needle can be placed in the non-flexed condition prior to linear advancement (i.e., advancement while rotating to produce a linear trajectory) so that the helical path cut by traditional kinked tip needle designs, and the resulting tissue damage, can be avoided.

From this, those skilled in the art will appreciate that the invention also relates to a method for steering the flex-tip surgical needle in body tissue. Referring to FIG. 7, the method 100 includes the step 102 of providing a steerable needle having a flex-tip configuration such as those of FIGS. 1-6. The method 100 also includes the step 104 of advancing the needle in the body tissue to cause tip flexure, the flexure causing the needle to follow a curved trajectory. The method 100 also includes the step 106 of rotating the needle about its longitudinal axis in place (without advancement) to remove the tip flexure. The method 100 further includes the step 108 of rotating the needle about its longitudinal axis while advancing the needle to cause the needle to follow a linear trajectory. The steps 104, 106, and 108 can be performed repeatedly and in any order selected to steer the needle along a desired path.

The flex-tip surgical needle 10, while suited for manual use, is especially well suited for robotic-assisted surgical procedures. Since the flex joint 16 operates in the manner described herein to help limit tissue damage when advanced along a linear trajectory, the need for the skilled physician's experience in detecting when damage is occurring or is likely to occur is diminished. This permits the operating physician to take advantage of the accuracy and precision that can be achieved through the use of robotic-assisted techniques while helping to minimize the risks.

Example Configuration

To measure the efficacy of the flex-tip needle construction, a needle having the general configuration illustrated in FIGS. 1-5 was prepared. The needle shaft was made from hollow tube nitinol having an outer diameter (OD) of 0.91 mm and an inner diameter (ID) of 0.60 mm. The beveled tip was made of the same material as the shaft, with the same OD (0.91 mm) and having a length of 4.0 mm long at its longest point. The tip had a bevel angle of 10°. The flex joint connecting the needle shaft and the tip was made of three 0.125-mm diameter nitinol wires laid side by side and oriented so that their least stiff direction coincided with the direction in which the bevel would naturally make the needle bend during tissue insertion, i.e., along the X-Z plane in FIGS. 1-5. The gap between the tip section and the needle shaft was approximately 0.15 mm, which allowed the tip to flex to a maximum angle of roughly 22°. A cold weld epoxy (J-B Weld™) was used to attach the wires of the flex joint to both the shaft and tip section. In this embodiment, since the tip was formed of tubular nitinol, the cold weld epoxy extended through the length of the tip and thereby formed a portion of the bevel.

The in-plane stiffness of the flexure joint (i.e., movement of the tip in the X-Z plane in FIGS. 1-5) was determined experimentally by hanging weights from the beveled tip using a drop of glue and a hook in 5g increments. The resulting stiffness for the flexure was approximately 3.6 mN·m/rad. The out-of-plane stiffness (i.e., movement of the tip in the X-Y plane in FIGS. 1-5) was determined to be 16.5 mN·m/rad using the same experimental procedure.

To assess the curved trajectory performance of the needle, a conventional kinked tip beveled needle was constructed using identical materials, i.e., tubular nitinol (0.91 mm OD×0.6 mm ID). A kinked tip was constructed from a stainless steel wire with a 0.91-mm OD, a bevel angle of 15°, and a kink angle of approximately 25° at a point 4 mm from the tip. When inserted into a phantom tissue (10% by weight Knox™ Gelatin), the flexure-tip needle was able to achieve a curved trajectory comparable to that of the kinked bevel-tip needle.

To explore whether the flexure-tip needle was capable of providing adjustable curvature via duty cycling, an experiment was performed in which the needle was inserted into a phantom tissue and a pork loin via a robot with a constant insertion velocity of 0.5 cm/s, and constant rotational velocity (during the periods of the duty-cycle when axial rotation occurs) of 4 rev/s. Insertions were performed with duty-cycle ratios of 0%, 20%, 33%, 50%, 66%, 80%, and 100% in the phantom tissue, and 0%, 25%, 50%, 75%, and 100% in pork loin, with 0% indicating no rotation, and 100% indicating constant rotation. When not rotating, the bevel orientation was always the same, such that the needle paths were all in the same plane. The radius of curvature for each duty-cycle ratio was determined by visually fitting a circle to the needle paths. The nominal radius of curvature of the flexure-tip needle ranged from zero at 100% duty cycle to a maximum (0% duty cycle) of 12.1 cm in phantom tissue, and 17.6 cm in ex vivo pork loin. The relation between the radius of curvature and duty cycle appeared substantially linear.

For a qualitative assessment of tissue damage caused by needle insertion using duty cycling, the kinked bevel-tip needle, a straight bevel-tip needle, and the flexure-tip needle were advanced into phantom tissue. The straight bevel-tip needle was a commercially available (Becton Dickinson and Co., NJ) 20 gauge spinal needle (OD 0.91 mm) with an 18° bevel angle. Each needle was inserted with a constant velocity of 0.5 cm/s, and constant axial velocity of 4 rev/s (that is, a duty cycle of 100%). After insertion, the needle was retracted using the same parameters with the intent of having its tip follow the same path as during insertion. Liquid dye was then injected into the insertion hole to visualize the needle path. Predictably, the spinning kinked bevel tip sliced through the tissue in a local helical pattern during insertion and thus produced tissue damage. The flex-tip needle, however, behaved in a manner similar to the straight bevel-tip needle and did not produce any further tissue damage.

From the above description of the invention, those skilled in the art will perceive improvements, changes and modifications. Such improvements, changes and modifications within the skill of the art are intended to be covered by the appended claims.

What is claimed is:

1. A steerable surgical needle comprising. an elongated needle shaft; a beveled tip portion; and a flexural element that connects the elongated needle shaft to the beveled tip portion, the flexural element permitting the beveled tip portion to deflect relative to the elongated needle shaft, wherein the beveled tip portion comprises a beveled surface, and wherein the beveled tip portion and flexural element are configured so that advancement of the surgical needle into tissue causes the tissue to apply normal forces to the beveled surface, the normal forces causing the flexural element to bend allowing the beveled tip portion to deflect, causing the surgical needle to cut a curved path through the tissue in response to further advancement in the tissue, and wherein the surgical needle is configured so that rotation of the elongated needle shaft about a longitudinal axis of the elongated needle shaft reduces the bend of the flexural element and the curvature of the path cut by the surgical needle.

2. The surgical needle of claim 1, wherein the elongated needle shaft is configured to follow the deflected beveled tip portion along curved trajectories through the tissue.

3. The surgical needle of claim 1, wherein the surgical needle is configured to follow a straight trajectory through the tissue when advanced while rotating about the longitudinal axis of the elongated needle shaft.

4. The surgical needle of claim 1, wherein the surgical needle is configured for duty cycling rotation of the surgical needle about the longitudinal axis of the elongated needle shaft during advancement in order to steer the surgical needle along a desired trajectory.

5. The surgical needle of claim 1, wherein the surgical needle is configured so that the beveled tip portion when deflected relative to the elongated needle shaft assumes a coaxial relation with the elongated needle shaft in response to rotation of the elongated needle shaft about the longitudinal axis of the elongated needle shaft.

6. The surgical needle of claim 1, wherein the flexural element has elastic properties selected such that the flexural element exhibits a resistance to bending that is less than a resistance to bending exhibited by the elongated needle shaft.

7. The surgical needle of claim 1, wherein the beveled tip portion has a non-deflected condition extending coaxially with the elongated needle shaft, and wherein the flexural element is deflectable so as to permit the beveled tip portion to deflect away from the non-defected condition.

8. The surgical needle of claim 1, wherein the beveled tip portion comprises a beveled surface, the flexural element being configured to permit bending in response to normal forces acting on the beveled surface in response to advancing the surgical needle in the tissue.

9. The surgical needle of claim 1, wherein the longitudinal axis of the elongated needle shaft extends along an X-axis of a 3-D space defined by X, Y, and Z axes, and wherein the flexural element is configured to permit free bending in an X-Z plane of the 3-D space and to inhibit bending in an X-Y plane of the 3-D space.

10. The surgical needle of claim 1, wherein advancement of the surgical needle into the tissue causes the flexural element to permit deflection of the beveled tip portion, which causes the surgical needle to follow a curved trajectory.

11. The surgical needle of claim 1, wherein advancement of the surgical needle into the tissue while simultaneously rotating the elongated needle shaft causes the flexural element to resist deflection of the beveled tip portion, which causes the surgical needle to follow a straight trajectory.

12. The surgical needle of claim 1, wherein advancement of the surgical needle into the tissue while duty cycling a simultaneous rotation of the elongated needle shaft causes the flexural element to permit limited deflection of the beveled tip portion, which causes the surgical needle to follow a curved trajectory that corresponds to the duty cycling.

13. The surgical needle of claim 1, wherein rotation of the elongated needle shaft about the longitudinal axis of the elongated needle shaft without advancement of the surgical needle causes the beveled tip portion to straighten from a deflected condition and extend coaxially with the longitudinal axis of the elongated needle shaft.

14. The surgical needle of claim 1, wherein the elongated needle shaft and beveled tip portion are spaced apart in relation to each other and the flexural element extends between and interconnects the elongated needle shaft and beveled tip portion.

15. The surgical needle of claim 1, wherein the flexural element is configured to be bendable in a first direction relative to the longitudinal axis of the elongated needle shaft and to resist bending in directions transverse to the first direction.

16. The surgical needle of claim 15, wherein the first direction is a direction that the beveled tip portion naturally bends during insertion of the surgical needle into the tissue due to its beveled configuration.

17. The surgical needle of claim 15, wherein the flexural element has a configuration of a beam that has a flexibility in a first plane that is substantially greater than its flexibility in a second plane that is perpendicular to the first plane.

18. The surgical needle of claim 1, wherein the flexural element comprises a plurality of flexural members arranged adjacent to each other and extending parallel to each other.

19. A steerable surgical needle comprising:

an elongated needle shaft;

a beveled tip portion; and a flexural element that connects the needle shaft to the tip portion, the flexural element permitting the tip portion to deflect relative to the needle shaft, wherein the beveled tip portion comprises a beveled surface, and wherein the tip portion and flexural element are configured so that advancement of the needle into tissue causes the tissue to apply normal forces to the beveled surface, the normal forces causing the flexural element to bend allowing the tip portion to deflect, causing the needle to cut a curved path through the tissue in response to further advancement in the tissue, wherein the flexural element comprises a plurality of round wires arranged adjacent to each other and parallel to each other in a coplanar relationship with each other.

20. The surgical needle of claim 1, wherein the flexural element comprises a plurality of flat bands arranged on top of each other.

21. The surgical needle of claim 1, wherein the flexural element is constructed of at least one of a stainless steel alloy and a nickel-titanium alloy, and a pliable material.

22. The surgical needle of claim 1, wherein the flexural element is configured to permit the beveled tip portion to deflect freely within a first plane that is parallel to the longitudinal axis of the elongated needle shaft and to inhibit deflection of the beveled tip portion in a second plane that is parallel to the longitudinal axis of the elongated needle shaft and perpendicular to the first plane.

23. A steerable surgical needle comprising: an elongated shaft; a beveled tip; and a flexible portion that permits the beveled tip to deflect in a first direction relative to the elongated shaft in response to forces acting on the beveled tip during the surgical needle insertion, the flexible portion resisting deflection in directions transverse to the first direction, and wherein the surgical needle is configured so that rotation of the elongated shaft about a longitudinal axis of the elongated needle shaft reduces the deflection of the beveled tip in the first direction.

24. The surgical needle of claim 23, wherein the flexible portion has a configuration of a beam that has a flexibility in a first plane that is substantially greater than its flexibility in a second plane that is perpendicular to the first plane.

25. A method for steering through body tissue, a surgical needle having an elongated needle shaft and a beveled tip that is deflectable relative to the elongated needle shaft, the method comprising the steps of: advancing the surgical needle in the body tissue to induce tip flexure which causes the surgical needle to follow a curved trajectory; and rotating the surgical needle about a longitudinal axis of the surgical needle to remove the tip flexure and thereby reduce curvature of the curved trajectory.

26. The method of claim 25, further comprising the step of rotating the surgical needle about the longitudinal axis of the surgical needle while advancing the surgical needle to cause the surgical needle to follow a linear trajectory.

27. The method of claim 25, wherein the step of advancing the surgical needle comprises duty cycling rotation of the surgical needle about the longitudinal axis of the surgical needle in order to produce a desired curved trajectory.

* * * * *